(12) United States Patent
Spira

(10) Patent No.: US 11,040,013 B2
(45) Date of Patent: Jun. 22, 2021

(54) COMPACTED POWDER

(71) Applicant: Sensidose AB, Sollentuna (SE)

(72) Inventor: Jack Spira, Tyresö (SE)

(73) Assignee: Sensidose AB, Sollentuna (SE)

( * ) Notice: Subject to any disclaimer, the term of this patent is extended or adjusted under 35 U.S.C. 154(b) by 212 days.

(21) Appl. No.: 15/775,667

(22) PCT Filed: Nov. 9, 2016

(86) PCT No.: PCT/EP2016/077161
§ 371 (c)(1),
(2) Date: May 11, 2018

(87) PCT Pub. No.: WO2017/081094
PCT Pub. Date: May 18, 2017

(65) Prior Publication Data
US 2018/0325823 A1 Nov. 15, 2018

(30) Foreign Application Priority Data
Nov. 12, 2015 (GB) .................................... 1520007

(51) Int. Cl.
*A61K 9/20* (2006.01)
*A61J 3/10* (2006.01)
*A61K 31/198* (2006.01)
*B30B 11/22* (2006.01)

(52) U.S. Cl.
CPC ............... *A61K 9/2072* (2013.01); *A61J 3/10* (2013.01); *A61K 9/2095* (2013.01); *A61K 31/198* (2013.01); *B30B 11/221* (2013.01)

(58) Field of Classification Search
CPC .. A61K 9/2072; A61K 9/2095; A61K 31/198; A61J 3/10; B30B 11/221
See application file for complete search history.

(56) References Cited

U.S. PATENT DOCUMENTS

| 4,493,822 A | 1/1985 | Tovey |
| 4,828,843 A | 5/1989 | Pich et al. |
| 10,781,031 B2 | 9/2020 | Desset-Brethes et al. |
| 2005/0263926 A1 | 12/2005 | Tazawa et al. |

FOREIGN PATENT DOCUMENTS

| EP | 1 058 660 B1 | | 4/2006 |
| WO | WO 2013/115743 | * | 8/2013 |
| WO | 2014/114943 A1 | | 7/2014 |

OTHER PUBLICATIONS

International Search Report and Written Opinion for corresponding Patent Application No. PCT/EP2016/077161 dated Jan. 26, 2017.

* cited by examiner

*Primary Examiner* — Genevieve S Alley
(74) *Attorney, Agent, or Firm* — Renner, Otto, Boisselle & Sklar, LLP

(57) ABSTRACT

The present invention is directed towards a compacted powder shaped to comprise: a) a substantially annular girdle having opposing circumferential edges, the girdle having a diameter (x); and b) a dome protruding from each of the opposing circumferential edges of the girdle, wherein the height of each dome (hd) from the circumferential edge is, individually, about 0.18x to about 0.28x.

16 Claims, 3 Drawing Sheets

COMPACTED POWDER

This application is a national phase of International Application No. PCT/EP2016/077161 filed Nov. 9, 2016 and published in the English language, which claims priority to United Kingdom Patent Application No. 1520007.4 filed Nov. 12, 2015, which are hereby incorporated herein by reference.

The present invention relates to a compacted powder, such as a tablet, shaped to provide for ease of dispensing from a device and/or efficiency of manufacture.

The drug therapies used to treat or otherwise control a number of chronic diseases such as, but not limited to, Parkinson's disease, epilepsy, cancer, depression, schizophrenia, attention deficit-hyperactivity disorder (ADHD) as well as other neurobehavioral disorders, diabetes, arthritis and asthma and diseases requiring anti-coagulants, anti arrhythmics and/or analgesia, often have a narrow therapeutic window and produce significant side effects when dosing is non-optimal.

The timing of doses as well as the amount of the dose is, therefore, critical to maintain drug levels within desired levels and it is important that administered doses are as accurate as possible to reduce the effects that can otherwise arise from over, under or imprecise dosing.

There are two main groups of dosage forms or preparations, the largest of which consists of medicines known as dosed medicines. Examples of such preparations are tablets, capsules, injection ampoules etc., where each preparation unit contains a predetermined dose of the active medical substance. The main advantage of dosed medicines is that the dosing of the medicine is built into the dosage form.

The second main group of dosage forms consists of non-dosed medicines, such as ointments, mixtures, powders, granulates etc. For such dosage forms, the quantity corresponding to the dose required in a specific case is taken out on each occasion of medicine administration. The main advantage of non-dosed forms is that in many cases the exact dose required for administration to a subject is specific to that patient and non-dosage forms allow tailored preparation of medicaments for administration to a person in need thereof. However, the dose must be calculated and prepared each time the dose is to be administered, which often requires specialist knowledge and equipment.

A frequent problem with the administration of a medicine is that the dose required for administration to a patient is known, but the choice of doses, in the form of tablets or capsules for example, is relatively limited. Frequently a tablet has to be broken in order to divide the original dose into halves or even into quarters. Despite this dividing up of the dose, uncertainty may still remain with regard to dose accuracy.

The listing or discussion of a prior-published document in this specification should not necessarily be taken as an acknowledgement that the document is part of the state of the art or is common general knowledge.

EP 1 058 660 B1 describes a procedure for dosing a medicine for dispensing to a single patient from a supply of equally large units or partial doses of the medicine in the form of single tablets or pellets where each unit or partial dose contains from approximately 2 to approximately 20 weight percent of the therapeutic total dose to be administered to the patient on a single occasion. Therefore, as each unit dose comprises only a small amount of the therapeutic total dose, doses may be tailored to patients more efficiently.

However, to render this procedure suitable for use by individual patients outside of a hospital environment, it is preferential for such patients to use a dosing and dispensing device that is portable and, therefore, considerably smaller than the dispensing devices typically used within hospitals and pharmacies to store and dispense medicines. Such devices typically contain a compartment to store unit doses of the medicine.

The miniaturisation associated with producing a portable dosing and dispensing device has been found to encourage the formation of bridges or other blocking formations of tablets having standard dimensions within the dosing and dispensing device, which impacts on the efficiency of any such device.

Tablets for use in such dispensers typically have a spherical shape and are produced via a method of placing the tablet composition in powder form in a lower mould portion after which an upper mould is placed on top and compressed. After compression, the upper mould is removed and a mechanical arm sweeps across the upper surface of the lower mould which knocks the compressed tablet out of the lower mould. However, due to the dimensions of the tablets currently manufactured in this way, a relatively high frequency of breakages occurs when the mechanical arm sweeps across the lower surface. This leads to an inefficient and costly manufacturing process as tablet residue remains in the lower mould after breaking and, as such, these moulds have to be cleaned by hand.

Furthermore, where tablets are required to be dispensed by a dispensing device the efficient dispensing of the tablets from that device is of great importance, particularly where the device is configured to deliver a plurality of tablets to provide a patient with a particular dose of medication. Jams within dispensing devices may prevent the dispensing of tablets and/or cause the tablets to be damaged, potentially reducing the dispensed dosage. Moreover, errors in the counting of the tablets upon their being dispensed from the device is to be avoided, again to ensure that the patient is delivered the correct dose.

The present invention seeks to solve these problems by providing a tablet which can be efficiently manufactured while also reducing and/or minimising jams, damage to the tablets and/or counting errors when the tablets are dispensed by a dispensing device.

In a first aspect, the present invention provides a tablet formed from a compacted powder and shaped to comprise:

a) a substantially annular girdle having opposing circumferential edges, the girdle having a diameter (x); and b) a dome protruding from each of the opposing circumferential edges of the girdle, wherein the height of each dome ($h_d$) from the circumferential edge is, individually, about 0.18x to about 0.28x.

It has been surprisingly found that tablets shaped as detailed above are less prone to breaking during the manufacturing process than the tablets of the prior art. Moreover, when tablets having the present dimensions are used in dispensing devices such as those described herein, the occurrence of jamming of the device and/or bridging or breakage of the tablets is reduced and the occurrence of miscounted tablets is minimised.

Also provided by the invention is a method for preparing such a tablet.

Preferably, the tablet comprises a pharmaceutical composition.

In a further embodiment, the tablet has a $h_d$ of between about 0.18x to about 0.25x, such as about 0.22x to about 0.25x, such as wherein the $h_d$ is between about 0.22x to about 0.27x, optionally wherein the $h_d$ is between about 0.23x to about 0.26x, preferably $h_d$ is about 0.25x. The $h_d$ of each dome may be different from one another. Preferably $h_d$ is essentially the same for both domes.

It is preferred that the girdle of the tablet has an axial height ($h_g$) of about 0.27x to about 0.7x, for example wherein $h_g$ is about 0.37x to about 0.7x, such as about 0.4x to about 0.7x, for example $h_g$ is between about 0.43x to about 0.62x, such as $h_g$ is between about 0.43x to about 0.54x, such as wherein $h_g$ is about 0.5x, preferably $h_g$ is about 0.43x.

In preferred embodiments, the total height (i.e. axial height to the girdle diameter) of the tablet ($h_p$) is between about 0.8x to about 1.3x, for example wherein $h_p$ is between about 0.8x to about 1.03x, such as $h_p$ is between about 0.8x to about 1x optionally $h_p$ is between about 0.86x to about 0.97x, for example wherein $h_p$ is between about 0.89x to about 0.97x, optionally wherein $h_p$ is between about 0.93x to about 1.03x, such as $h_p$ is about 0.93x, preferably $h_p$ is about 1x.

In a further embodiment, x is between about 1 mm to about 5 mm, for example x is between about 2 to about 4 mm, preferably x is about 3 mm.

In an embodiment, x is about 3 mm, $h_d$ is between about 0.18x to about 0.28x and $h_g$ is between about 0.37x to about 0.62x, such as x is about 3 mm, $h_d$ is between about 0.18x to about 0.25x and $h_g$ is between about 0.43x to about 0.62x, for example, x is about 3 mm, $h_d$ is between about 0.22x to about 0.25x and $h_g$ is between about 0.43x to about 0.54x, preferably, x is about 3 mm, $h_d$ is about 0.25x and $h_g$ is about 0.43x.

In another embodiment x is about 3 mm, $h_d$ is between about 0.23x to about 0.28x and $h_g$ is between about 0.37x to about 0.62x, such as x is about 3 mm, $h_d$ is between about 0.23x to about 0.27x and $h_g$ is between about 0.43x to about 0.62x, for example, x is about 3 mm, $h_d$ is between about 0.24x to about 0.26x and $h_g$ is between about 0.43x to about 0.54x, preferably, x is about 3 mm, $h_d$ is about 0.25x and $h_g$ is about 0.43x.

In some preferred embodiments, $h_d$ is between about 0.55 mm to about 0.85 mm, such as between about 0.55 mm to about 0.75 mm, optionally $h_d$ is between about 0.65 mm to about 0.75 mm, preferably $h_d$ is about 0.75 mm.

In another embodiment, $h_g$ is between about 1.1 mm to about 2.1 mm, such as wherein $h_g$ is between about 1.2 mm to about 2.1 mm, optionally wherein $h_g$ is between about 1.3 mm to about 1.9 mm, for example wherein $h_g$ is between about 1.3 mm to about 1.62 mm, preferably wherein $h_g$ is about 1.3 mm.

In a further embodiment, the $h_p$ of the compacted powder is between about 2.4 mm to about 3 mm, optionally $h_p$ is between about 2.6 to about 2.9 mm, for example $h_p$ is between about 2.7 to about 2.9 mm, preferably $h_p$ is about 2.8 mm.

In another embodiment, the $h_p$ of the compacted powder is between about 2.4 mm to about 3.2 mm, optionally $h_p$ is between about 2.6 to about 3.1 mm, for example $h_p$ is between about 2.7 to about 2.9 mm, preferably $h_p$ is about 2.8 to 2.9 mm.

In an embodiment, x is about 3 mm, $h_d$ is between about 0.55 mm to about 0.85 mm and $h_g$ is between about 1.1 mm to about 1.86 mm, such as x is about 3 mm, $h_d$ is between about 0.55 mm to about 0.75 mm and $h_g$ is between about 1.3 mm to about 1.86 mm, for example, x is about 3 mm, $h_d$ is between about 0.65 mm to about 0.75 mm and $h_g$ is between about 1.3 mm to about 1.62 mm, preferably, x is about 3 mm, $h_d$ is about 0.75 mm and $h_g$ is about 1.3 mm.

In another aspect of the invention, there is provided a tablet comprising a pharmaceutical composition and formed from a compacted powder and shaped to comprise:

a largest cross section which is substantially circular in form and having a diameter x and at least one circumferential edge; and a pair of opposing domes extending from the circumferential edge, wherein the total height ($h_p$) of the tablet in a direction perpendicular to the plane of the largest cross section is less than 0.95x and equal to or greater than 0.86x.

In this aspect, it is preferred that $h_p$ is less than 0.95x and equal to or greater than 0.89x, optionally wherein $h_p$ is less than 0.94x and equal to or greater than 0.89x, for example wherein $h_p$ is less than 0.94x and equal to or greater than 0.92x, preferably wherein $h_p$ is 0.93x.

Preferably, the largest cross section comprises part of a substantially cylindrical girdle having a pair of opposed circumferential edges, wherein each of the opposed domes extends from one of the opposed circumferential edges. Preferably, the height of each dome ($h_d$) from the circumferential edge is, individually, about 0.18x to about 0.28x, e.g. as is described above.

In an embodiment, the hardness of the tablet is greater than about 2 kPa, for example greater than about 3 kPa or 4 kPa. Preferably, the tablet has a hardness of between about 2 kPa and about 6 kPa, optionally the tablet has a hardness of between about 2.5 kPa to about 5 kPa, for example the tablet has a hardness of between about 3 kPa and about 4.5 kPa, preferably the tablet has a hardness of between about 4 kPa and about 4.5 kPa.

It has been found that the hardness of the tablet, for example along with its shape, may provide a secondary influence to the frequency of the tablets breaking during the manufacturing process as well as the resistance of the tablets to break-up during storage and dispensing such as in a dispensing device. In order to increase efficiency and reduce production time and costs, it is desirable to produce a tablet which is less prone to breaking during the manufacturing process and dispensing process using an automatic dispenser. Importantly, broken tablets do not only jam the dispensing device but also lead to errors in dosing when being taken by a patient as less active ingredient is comprised within the tablet than required.

In an embodiment, the tablet has a pseudo-spherical or modified ball shape.

In another embodiment, the tablet has a total mass of between about 5 mg to about 100 mg, such as about 10 mg to about 80 mg, optionally about 15 mg to 50 mg, preferably the total mass of the compacted powder is 20 mg.

In a further embodiment, the tablet is a micro-tablet.

In a further aspect, the invention provides a mould configured to produce a tablet as detailed herein. For example, the mould may comprise two opposing mould halves configured to correspond to each half of the shaped tablet. Placing a powder composition in the moulds and compressing the moulds leads to a tablet as detailed herein. Such a mould may be configured for use in direct compression moulding.

In another aspect the invention provides a method for preparing a tablet as detailed above.

Such a method may comprise the steps of:
a) providing a powder composition; and
b) shaping the powder The shaping step may be done by any method known in the art. However, preferably the shaping step comprises the method of direct compression moulding. For example, the method may include a step of filling a mould as detailed herein with a powder composition. The two halves of the mould may then be compressed so as to result with a tablet of desired hardness. Application of a pressure in the region of 12 kN to 13 kN (e.g. around 12.4 kN) may be regarded as generally sufficient to achieve the preferred hardness characteristics of the present invention.

In another aspect, the invention provides the use of a dispensing device to dispense the compacted powder tablets detailed herein. Preferably the device is a medication dispensing device.

Such a device may comprise a removable cassette. Ideally, the tablets are stored in the removable cassette. Preferably, the removable cassette is configured to be able to store between about 50 to about 1500 tablets, such as between about 250 to about 750 tablets, optionally between about 500 to about 750 tablets, preferably wherein the cassette is configured to store about 750 tablets.

Preferably, when using the device detailed above, the probability of encountering a dispensing error is equal to or less than about 2%, optionally wherein the probability is equal to or less than about 1%, such as wherein the probability is equal to or less than about 0.5%, for example wherein the probability is equal to or less than about 0.05% preferably wherein the probability is equal to or less than about 0.13% or less than about 0.013%.

In a further aspect, the invention provides a method of using a device as detailed above for dispensing a tablet according to the invention.

In a further aspect, the invention provides a dosing and/or dispensing device comprising a storage chamber containing a plurality of tablets as described herein. Preferably, the storage chamber is comprised within a removable cassette.

In a further aspect, the invention provides a cassette configured to be releasably engageable in a dosing and/or dispensing device, wherein the cassette comprises a storage chamber which contains a plurality of tablets as detailed herein. Preferably the cassette is for single use.

The devices for dispensing tablets as described herein may be comparable in size with hand held devices. The device or cassette preferably comprises a feed assembly configured to dispense individual tablets. Typically, the dispensing apparatus comprises a plurality of feed pockets for transporting the tablets. This may be in the form of a feed wheel comprising pockets, which are configured to each receive an individual tablet. Preferably, the feed pockets have a depth of around x to around 1.3x, for example around x to around 1.1x, e.g. of about x. On rotating the feed wheel the tablets are released into a dispensing chamber.

Preferred embodiments of the invention will now be described by reference to the following drawings.

Figure 1:
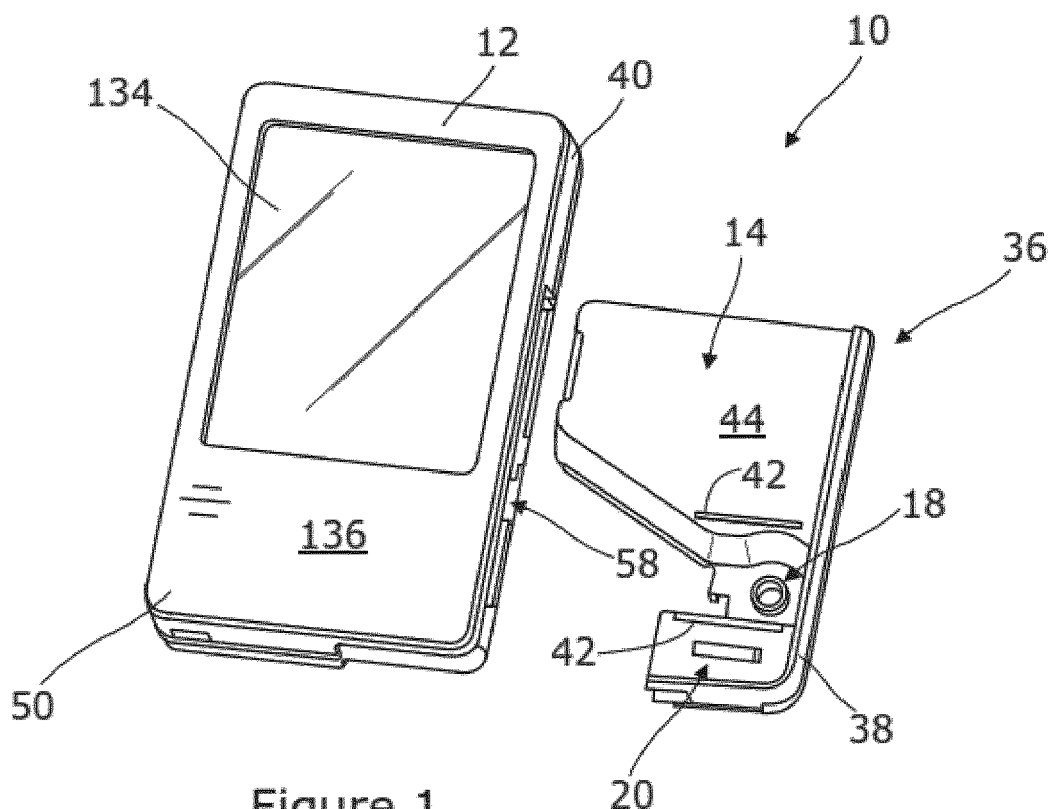
FIGS. 1 and 2 show a device for dispensing tablets according to the present invention.
Figure 2:
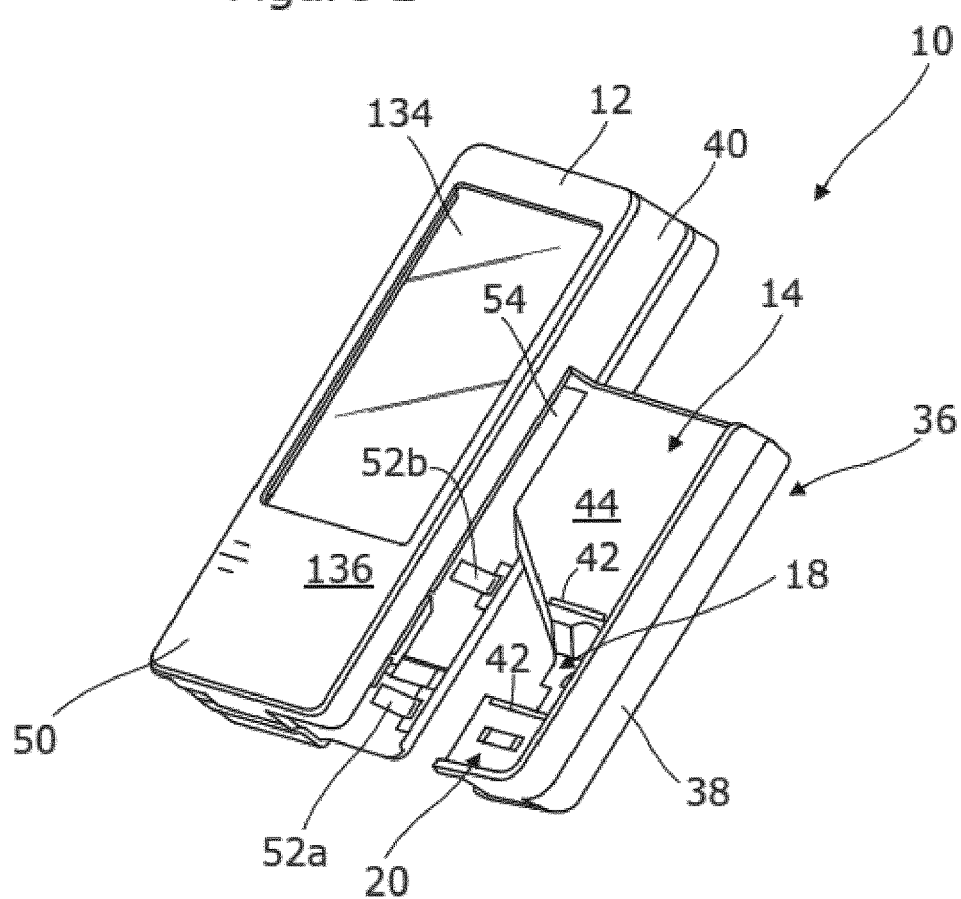

Embodiments of the present invention relate to tablets for use with medicine dispensing devices. An example of a medicine dosing and dispensing device 10 is shown in FIGS. 1 and 2.

The dosing and dispensing device 10 may be comparable in size with hand held devices such as, for example, mobile telephones, thereby rendering the dosing and dispensing device 10 suitable for use as a hand held device. It is envisaged that in other embodiments the size and shape of the dosing and dispensing device 10 may be varied to render the dosing and dispensing device 10 suitable for users having limited dexterity, for example. The device 10 may also be sized and designed to be used in a fixed location.

The dosing and dispensing device 10 includes a housing 12 including a storage chamber 14 to store discrete units or tablets of medicine 16 and a feed assembly 18 located between the storage chamber 14 and a dispenser 20. In some embodiments, the dosing and dispensing device 10 also includes an impacter 22 (see FIG. 3) that is operably associated with the storage chamber 14 to agitate units of medicine 16 stored in the storage chamber 14.

Figure 3:
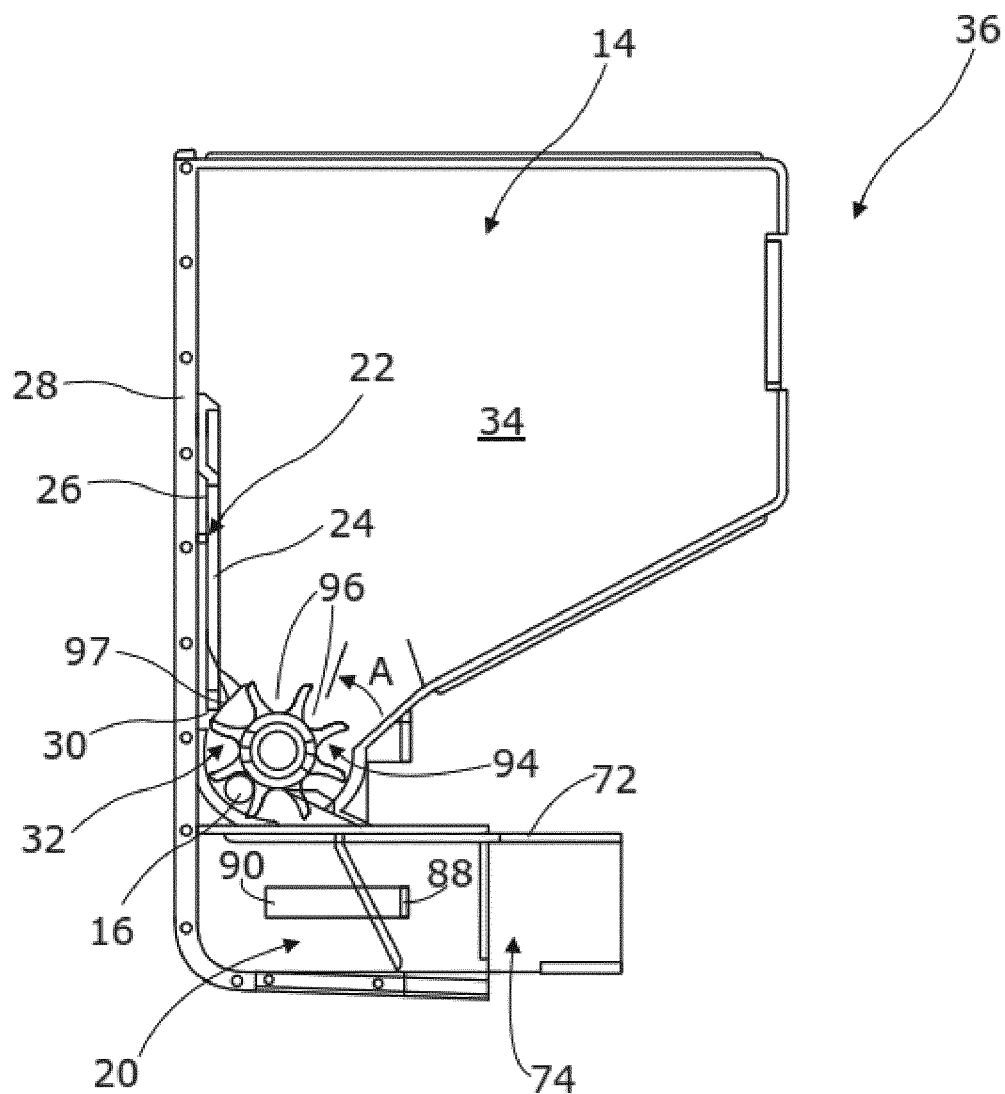
FIG. 3 shows a cassette for use with a device for dispensing tablets according to the present invention.

As can be seen from FIG. 3, the impacter 22 includes a rigid element 24 fixedly connected at one end 26 to a wall 28 inside of the storage chamber 14. The impacter 22 is operably associated at a second end 30 with an actuating mechanism 32 that deflects the second end 30 of the impacter 22 towards the wall 28 of the storage chamber 14 to strain the impacter 22 such that, when released, the strained impacter 22 moves towards the interior 34 of the storage chamber 14 and impacts again units of medicine 16 stored therein.

The example dosing and dispensing device 10 includes a storage chamber 14 provided in a removable cassette 36 that is releasably engageable with the housing 12.

In other embodiments of the invention it is envisaged that the storage chamber 14 may be permanently located within the housing 12, the housing 12 including an opening to permit access to the storage chamber 14 to permit refilling thereof.

The housing 12 and cassette 36 may include mutually engageable latch members that interengage on insertion of the cassette 36 into the housing 12 to retain the cassette 36 within the housing 12. The dosing and dispensing device 10 also includes an ejection mechanism that is selectively operable to disengage the latch members and allow removal of the cassette 36 from the housing 12.

This allows the provision of a cassette 36 that, when received in the housing 12, has an external surface 38 that sits flush with an adjacent outer surface 40 of the housing 12, which enhances the appearance of the dosing and dispensing device 10.

The latch members include elongate projections 42 provided on an upper face 44 of the cassette 36 and extending in the direction in which the cassette 36 is inserted into and withdrawn from the housing 12.

The latch members also include correspondingly shaped and sized openings 46 (FIGS. 9 and 10) provided on an inner surface 48 of an upper face 50 of the housing 12. The openings 46 are located on the inner surface 48 so as to be aligned with the projections 42 provided on the cassette 36. When the cassette 36 is fully inserted into the housing 12, an interference fit is formed to prevent sliding withdrawal of the cassette 36 from the housing 12.

In other embodiments, alternative means of securing the cassette 36 into the device 10 as may be known in the art may be utilized.

The feed assembly 18 includes a feed wheel 94 (FIG. 3) defining a plurality of feed pockets 96 about its circumference. The feed wheel 94 is located in the cassette 36 between the storage chamber 14 and the dispenser 20 and comprises seven pockets 96 and one blank pocket 97. The feed wheel comprises a central hub and pairs of equally spaced parallel radially extending fingers to form the pockets 96 therebetween. The pockets 96 are sized so as to contain a single tablet 16. The blank pocket 97 is of similar dimensions as the pockets 96 but is formed from a pair of radially extending lugs 99 which acts as a baffle to the receipt and/or containment of a tablet 16 in that part of the feed wheel 94.

The feed wheel 94 is mounted to rotate so that rotation in a first direction moves the feed pockets 96 sequentially into alignment with a feed channel of the storage chamber 14 to each receive a unit of medicine 16.

On further rotation of the feed wheel 94 in the first direction, the feed pockets 96 are moved sequentially into alignment with an inlet of the dispensing chamber 72 of the dispenser 20 to feed the respective units of medicine 16 into the dispensing chamber 72 dispenser 20.

Typically, the device 10 will contain a system of sensors and a controller (not shown) for operating the feed wheel 94 to dispense a quantity of tablets as programmed and/or for counting the number of tablets which are dispensed by the device to ensure that a particular dispensing program is properly executed.

Spherical or pseudo-spherical tablets have been found to be suitable for use in such devices, which are ideal for tailoring doses of pharmaceuticals by the person requiring the treatment rather than a trained medical practitioner. Depending on a person's weight, severity of condition etc. the required dose of a pharmaceutical medicament for that person will be specific to them. As each tablet contains only a small amount of the pharmaceutical dose, the dose to be taken by the person in need thereof may be made more exact by using tablets according to the invention. As such, depending on the dose required, a relatively large number of tablets may need to be dispensed and administered to the patient per dose cycle, such as 5, 10, 15, 20 or 25 units, or any discrete number between these values. Indeed, the number of tablets to be dispensed and administered to the patient per dose cycle may be greater than 25, greater than 50 or greater than 100. Therefore, at each interval of administration, a relatively large number of tablets will need to be dispensed from the device at any one time.

As a number of tablets may need to be dispensed from the device at each dosing time, a large number of tablets are required to be stored within the device. For ease of use and to lower the occurrence of cross-contamination, it is desirable that these tablets be stored in a removable cassette. Ideally, each cassette will house a relatively large number of tablets so as to reduce the frequency of changing the cassette. Preferably, the removable cassette is configured to be able to store between about 50 to about 1500 tablets, such as between about 250 to about 750 tablets, optionally between about 500 to about 750 tablets, preferably wherein the cassette is configured to store about 750 tablets.

However, when such a large number of tablets are stored together the chances of forming bridges of tablets or other jams within the device are increased, which leads to blockages within the storage chamber and therefore potentially inaccurate and/or incomplete dosing or malfunctioning of the device.

Spherical or pseudo-spherical tablets are produced via a number of methods. However, an effective and efficient process is to place the powder in a lower mould and place an opposing upper mould on top. These moulds are then compacted together at a desired force after which, the upper mould is removed. A mechanical arm then sweeps across the upper surface of the lower mould essentially knocking the compacted powder out of the mould.

Sometimes, when being removed from the mould the tablets break or crumble, which leads to a less efficient manufacturing process, wasted material and higher manufacturing costs.

It has been surprisingly found that the dimensions and hardness of the tablets have been found to significantly influence the number of breakages occurring during their production via the method as detailed above.

The breaking of tablets has two significant drawbacks. Firstly, broken tablets will comprise less mass, and therefore less pharmaceutical dose, than required and predicted. As such, this can lead to dosing errors, particularly under dosing, when administering such tablets to a patient. Secondly, when the tablets are broken during production, a large amount of the powder residue remains in the lower mould. As a result, these moulds need to be cleaned and emptied manually before they can be used again. Therefore, as the number of breakages occurring during manufacture increases, the costs of manufacture increase and the efficiency decreases.

Figure 4:
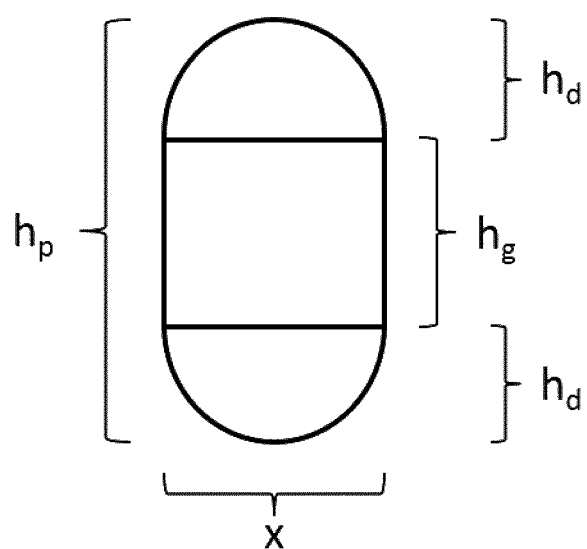
FIG. 4 shows a tablet according to the invention.

The present invention addresses these problems by providing a formed from a compacted powder as shown in FIG. 4, being shaped to comprise: a substantially annular girdle having opposing circumferential edges, the girdle having a diameter (x); and a dome protruding from each of the opposing circumferential edges of the girdle, wherein the height of each dome ($h_d$) from the circumferential edge is, individually, about 0.18x to about 0.28x. The values of $h_d$ and the overall height of the tablet ($h_p$) and the girdle ($h_g$) are variable as is described herein.

The tablets of the invention preferably comprise a pharmaceutical dose. In order to tailor the dose of a pharmaceutical dose to a patient, it is desirable that each tablet comprises only a small portion of the required dose. For example, drug therapies used to treat Parkinson's disease, epilepsy, cancer, depression, schizophrenia, attention deficit-hyperactivity disorder (ADHD) as well as other neurobehavioural disorders, diabetes, arthritis and asthma and diseases requiring anti-coagulants, anti arrhythmics and/or analgesia, often have a narrow therapeutic window and produce significant side effects when dosing is non-optimal. Accordingly, the tablets of the invention may include medicaments such as levodopa/carbidopa or levodopa/benserazide, morphine, oxikodone or methadone, pregabaline, diazepam, oxazepam or alprazolam, methylfenidate, acarbose, metformine, glibenclamide or glipizide, atomoxetine, capecitabine, pyridostigmine, warfarin, valproate or quetiapine (as appropriate, i.e. depending on the disease to be treated).

As such, it is preferable for each tablet to comprise only a small amount of the total pharmaceutical dose to be administered. For example, the amount of pharmaceutical dose comprised in each tablet may be between about 1 wt % to about 20 wt % of the total dose required, such as between about 1 wt % to about 10 wt %, for example between about 2 wt % to about 5 wt %.

The invention will now be illustrated by the following non-limiting Examples.

EXAMPLES

Example 1

The dispensing of various compacted powders was assessed using a MyFID (Sensidose AB, Sollentuna, Sweden) device.

The tablets were composed of levodopa (5 mg), carbidopa (1.25 mg) and excipients in an amount sufficient to bring the total weight of each tablet to 20 mg.

Various compacted powders were tested for their efficacy when in use in the MyFID device (see Table 1). Discrete units of the compacted powders were loaded into a removable cassette, which was inserted into the MyFID device.

The device was then set to dispense the discrete units of compacted powder. The dispensing order was random and in each round 5, 10, 15 or 20 units of compacted powder were dispensed. The number of compacted powder units actually dispensed was compared to the number of units programmed to be dispensed. The number of broken compacted powder units or number of occasions where dispensing could not be performed by the device due to the tablet causing technical faults such as bridging, were also counted. The breaking of compacted powder units occurs during the manufacture of the units and is dependent on the dimensions and hardness of the units. In all of the compacted powders x is 3 mm. The average weight of each of the compacted powders is 20±1 mg.

The results of the assessment are detailed below in Table 1.

TABLE 1

| $h_d$ [as function of x] | $h_p$ [as function of x] | Hardness (kPa) | Bridging Occasions | Occurrence of breaking | Occurrence of wrong dosing |
|---|---|---|---|---|---|
| 0.18x | 0.97x | 2 | 56.9% | 22.2% | 8.3% |
| 0.18x | 0.86x | 4.2 | 23.8% | 28.6% | 3.2% |
| 0.22x | 0.97x | 2.5 | 28% | 14.6% | 6.7% |
| 0.22x | 0.89x | 3.9 | 9.6% | 0% | 0% |
| 0.25x | 0.93x | 4.3 | 1.8% | 0% | 0% |
| 0.29x* | 0.85x | 4.3 | 8.7% | 0.3% | 0.3% |

*Comparative example

These results show that for compacted powders having a $h_d$ of 0.18x, the occurrence of breakages is not significantly influenced when the hardness is increased from 2 kPa to 4.2 kPa. However, the bridging occurrence is reduced when the hardness is increased.

For compacted powders having a $h_d$ of 0.22x, the occurrence of breakages is significantly reduced when the hardness is increased from 25 kPa to 39 kPa. Similarly, the occurrence of bridging is also reduced.

Increasing the $h_d$ from 0.22x to 0.25x and keeping the hardness at around 40 kPa, the occurrence of bridging increases even further leading to highly accurate dispensing of the compacted powders.

Increasing the $h_d$ further from 0.25x to 0.29x leads to an increase in the number of breakages, which in turn would lead to an inaccurate dosing of any pharmaceutical composition comprised within the compacted powder unit.

As the hardness of the compacted powder increases from about 20 kPa to about 40 kPa, the occurrence of tablets breaking significantly lowers for compacted powders having a $h_d$ of between about 0.22x and about 0.75x.

However, the dimensions of the compacted powders appear to be the primary influence of the number of breakages that occur. For compacted powders having a $h_d$ of 0.18, it was found that then number of breakages was not significantly influenced by the hardness of the powders and that the number of breakages was, therefore, due to the dimensions of the compacted powders rather than their hardness. Without wishing to be bound by any particular theory, it is postulated that reductions of breakages would be shown for tablets having dimensions of the invention when compared to the prior art, notwithstanding any change in hardness.

Surprisingly, it was found that for the production of compacted powders having a $h_d$ of 0.29x, the number of breakages increases compared to compacted powders having the same hardness but lower $h_d$, particularly a $h_d$ of 0.25x. Without wishing to be bound by theory, it is believed that as the compacted powders pass a certain $h_d$ value and become more spherical, the portion of powder encased by the lower mould increases to the overall volume of the compacted powder. This means that the compacted powders require more force to remove them from the moulds and this, in turn, leads to a large number of breakages.

These results also show that the dimensions of the tablets influence the occurrence of the formation of tablet bridges within the storage cassette. In particular, it has been found that as $h_d$ increases from 0.18x to 0.25x, the number of bridging occasions decreases to 1.8%. However, as $h_d$ increases further to 0.29x the number of bridging occasions increases to 8.7%. Therefore, it has been found that when using tablets having a $h_d$ of 0.25x, the number of bridging occasions significantly decreases. However, as $h_d$ is increased further, and thus making the tablets more spherical, the number of bridging occasions surprisingly begins to rise.

No doubt many other effective alternatives will occur to the skilled person. It will be understood that the invention is not limited to the described embodiments and encompasses modifications apparent to those skilled in the art lying within the spirit and scope of the invention.

The invention claimed is:

1. A tablet formed from a compacted powder comprising a pharmaceutical composition and shaped to comprise:
  a) an annular girdle having opposing circumferential edges, the girdle having a diameter (x) and a cross section; and
  b) a dome protruding from each of the opposing circumferential edges of the girdle, wherein the height of each dome ($h_d$) from the circumferential edge is, individually, about 0.22x to about 0.25x;
  c) a total height ($h_p$) of the tablet in a direction perpendicular to the plane of the girdle cross section which is about 0.89x to about 0.93x.

2. The tablet according to claim 1, wherein $h_p$ is 0.93x.

3. The tablet according to claim 1 wherein the $h_d$ is between about 0.23x to about 0.25x, optionally wherein $h_d$ is about 0.25x, optionally wherein $h_d$ is either different or the same for each of the dome protrusions, and optionally wherein $h_d$ is the same.

4. The tablet according to claim 1, wherein the girdle has a height ($h_g$) of about 0.27x to about 0.7x, optionally wherein $h_g$ is about 0.37x to about 0.7x, optionally wherein $h_g$ is between about 0.4x to about 0.7x, optionally wherein $h_g$ is between about 0.43x to about 0.62x, optionally wherein $h_g$ is between about 0.43x to about 0.54x, optionally wherein $h_g$ is about 0.5x, and optionally wherein $h_g$ is about 0.43x.

5. The tablet according to claim 4, wherein $h_d$ is about 0.25x and $h_g$ is between about 0.43x to 0.54x, and optionally wherein $h_d$ is about 0.25x and $h_g$ is about 0.43x.

6. The tablet according to claim 1, wherein $h_d$ is between about 0.55 mm to about 0.85 mm, optionally wherein $h_d$ is between about 0.55 mm to about 0.80 mm, optionally wherein $h_d$ is between about 0.65 mm to about 0.78 mm, and optionally wherein $h_d$ is about 0.75 mm.

7. The tablet according to claim 1, wherein $h_p$ is between about 2.4 mm to about 3.9 mm, optionally wherein $h_p$ is between about 2.4 mm to about 3.2 mm, optionally wherein $h_p$ is between about 2.6 mm to about 3.1 mm, optionally wherein $h_p$ is between about 2.7 mm to about 3.1 mm, optionally wherein $h_p$ is about 2.8 to 3.1 mm, and optionally wherein $h_p$ is between about 2.8 mm to about 2.9 mm.

8. The tablet according to claim 1 having a hardness of between about 2 kPa and about 6 kPa, optionally wherein the compacted powder has a hardness of between about 2.5 kPa to about 5.0 kPa, optionally wherein the compacted powder has a hardness of between about 3 kPa and about 4.5 kPa, and optionally wherein the compacted powder has a hardness of between about 4 kPa and about 4.5 kPa.

9. The tablet according to claim 1, wherein x is between about 1 mm to about 5 mm, optionally wherein x is between about 2 to about 4 mm, and optionally wherein x is about 3 mm.

10. The tablet according to claim 1 comprising a medicament selected from one or more of levodopa/carbidopa or levodopa/benserazide, morphine, oxycodone or methadone, pregabaline, diazepam, oxazepam or alprazolam, methylfenidate, acarbose, metformine, glibenclamide or glipizide, atomoxetine, capecitabine, pyridostigmine, warfarin, valproate or quetiapine.

11. A method for preparing a tablet, the method comprising the steps of:
  a) providing a powder composition; and
  b) shaping the powder to produce a tablet according to claim 1.

12. A device for dosing and/or dispensing medication, the device comprising a storage chamber containing a plurality of tablets according to claim 1.

13. A device according to claim 12, wherein the storage chamber is comprised in a removable cassette.

14. The device according to claim 13 comprising a feed assembly for dispensing tablets from the storage chamber, the feed assembly comprising a plurality of movable feed pockets for transporting the tablets.

15. The device or cassette according to claim 14, wherein the depth of the feed pockets is between about x and about 1.3x.

16. A cassette configured to be releasably engageable with a device for dosing and/or dispensing medication, the cassette comprising a storage chamber containing a plurality of tablets according to claim 1, such that the tablets may be dispensed from the storage chamber by the device.

* * * * *